United States Patent
McKenna

(10) Patent No.: US 6,899,459 B1
(45) Date of Patent: May 31, 2005

(54) BUCKY PRESENTATION ASSEMBLY FOR PATIENT TABLE

(75) Inventor: Gilbert W. McKenna, Revere, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/622,561

(22) Filed: Jul. 18, 2003

Related U.S. Application Data

(60) Provisional application No. 60/396,799, filed on Jul. 18, 2002.

(51) Int. Cl.⁷ .............................. G03B 42/04; A61B 6/04
(52) U.S. Cl. ........................ 378/181; 378/177; 378/209
(58) Field of Search ................................ 378/181, 209, 378/167, 195, 196, 177; 312/323; 108/6, 93, 143

(56) References Cited

U.S. PATENT DOCUMENTS

| | | | |
|---|---|---|---|
| 3,967,126 A | * | 6/1976 | Otto, Jr. ..................... 378/177 |
| 4,039,836 A | | 8/1977 | Shaw |
| 4,063,100 A | | 12/1977 | Williams |
| 4,139,776 A | * | 2/1979 | Hellstrom ................... 378/181 |
| 4,205,233 A | * | 5/1980 | Craig et al. ................. 378/209 |
| 4,982,419 A | | 1/1991 | Horikawa |
| 5,305,369 A | | 4/1994 | Johnson et al. |
| 5,475,885 A | * | 12/1995 | Ishikawa ........................ 5/601 |
| 6,341,893 B1 | * | 1/2002 | Matsumoto et al. ........ 378/209 |
| 6,450,684 B2 | * | 9/2002 | Kobayashi ................... 378/177 |
| 2001/0022833 A1 | * | 9/2001 | Kobayashi ................... 378/177 |
| 2001/0040939 A1 | * | 11/2001 | Kobayashi ................... 378/177 |

* cited by examiner

*Primary Examiner*—Michael Safavi
(74) *Attorney, Agent, or Firm*—McDermott Will & Emery LLP

(57) ABSTRACT

A patient table including a table assembly and a bucky presentation assembly including at least one rail secured to the assembly, a runner slidably received on the rail, a bucky, and a hinge pivotally connecting the bucky to the runner.

20 Claims, 5 Drawing Sheets

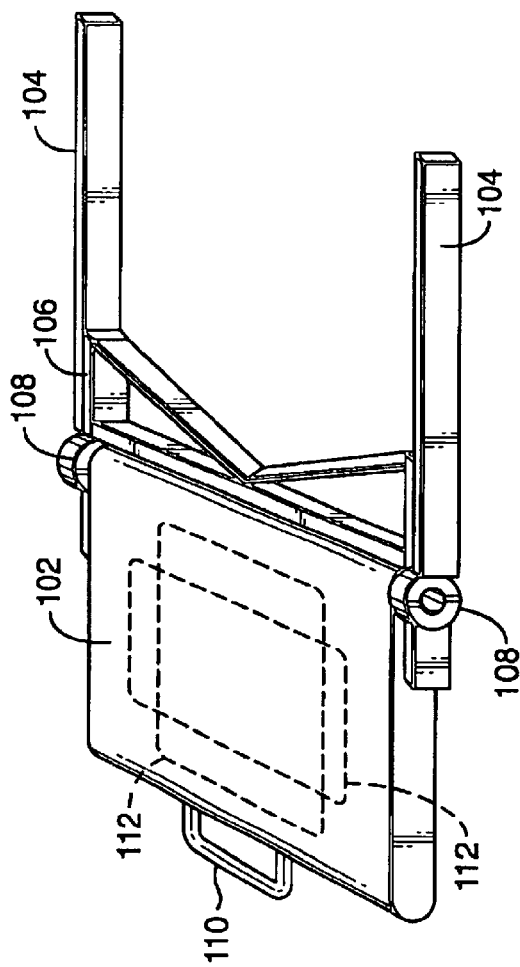
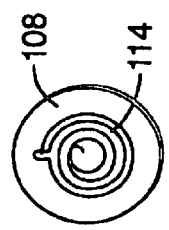
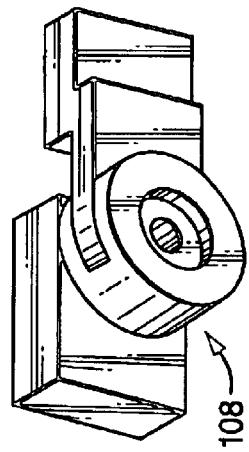

BUCKY PRESENTATION ASSEMBLY FOR PATIENT TABLE

CROSS REFERENCE TO RELATED APPLICATIONS

The present application claims priority to provisional U.S. patent application Ser. No. 60/396,799, filed on Jul. 18, 2002, which is assigned to the assignee of the present application and incorporated herein by reference.

FIELD OF THE DISCLOSURE

The present disclosure relates generally to tomography systems and, more particularly, to a table for supporting a sample, such as a patient, in a tomography scanner during a scanning procedure. Even more particularly, the present disclosure relates to a bucky for such a table and an assembly for positioning the bucky with respect to a patient supported on the table.

BACKGROUND OF THE DISCLOSURE

One of the most effective ways to reduce scattered radiation from an object being radiographed is through the use of a Potter-Bucky diaphragm. More commonly known as a 'bucky', this is an assembly which is normally located under the table of a diagnostic x-ray set and holds the x-ray film cassette and the secondary radiation grid. The grid is used to prevent secondary x-ray emission from the patient from reaching the x-ray film, and is formed from a large number of thin strips of lead separated by a radiolucent material. To prevent the outline of the grid from appearing on the film a mechanism is provided for moving the grid during exposure.

The bucky can be mounted on bearings which permit movement along rails under the x-ray table so that the grid and film can be moved to an appropriate position under the patient. The bucky is used with most diagnostic x-ray equipment.

What is still desired, however, is a new and improved bucky presentation assembly for use with medical diagnostic imaging and scanner systems. In particular, what is desired is a new and improved bucky presentation assembly that allows a bucky to be moved about a patient table and placed in multiple positions about the table. Among other features and advantages, the new and improved bucky presentation assembly will allow specific portions of a patient lying on the table to be quickly and accurately x-rayed. For example, the bucky presentation assembly will allow a hip of a patient lying or sitting on the table to be quickly and accurately x-rayed.

SUMMARY OF THE DISCLOSURE

The present disclosure provides a new and improved bucky presentation assembly for a patient table. A presentation assembly constructed in accordance with the present disclosure can be used for, but is not limited to, positioning a bucky with respect to a patient supported on the patient table.

According to one exemplary embodiment of the present disclosure, a patient table includes a table assembly and a bucky presentation assembly including at least one rail secured to the table assembly, a runner slidably received on the rail, a bucky, and a hinge pivotally connecting the bucky to the runner.

According to one aspect of the present disclosure, the at least one rail of the bucky presentation assembly comprises two spaced-apart, parallel rails, and one of the runners is slidably received on each rail. According to another aspect, the rails of the bucky assembly extend in a lateral direction with respect to the table assembly so that the bucky can be extended laterally out of a side of the table.

According to a further aspect of the present disclosure, the table also includes a turntable having a non-rotating portion secured to the table assembly, and a rotating portion rotatably mounted on the non-rotating portion. The rail of the bucky presentation assembly is secured to the rotating portion, so that the bucky presentation assembly can also be rotated, in addition to moved on the rail and pivoted up on the hinge. According to another aspect, the non-rotating portion of the turntable is linearly movable on the table assembly.

Among other features and advantages, a new and improved bucky presentation assembly constructed in accordance with the present disclosure allows specific portions of a patient lying on a patient table to be quickly and accurately x-rayed. For example, the bucky presentation assembly allows a hip of a patient lying or sitting on the table to be quickly and accurately x-rayed.

The foregoing and other features and advantages of the present disclosures will become more readily apparent from the following detailed description of the disclosure, as illustrated in the accompanying drawing.

BRIEF DESCRIPTION OF THE DRAWINGS

FIG. 2 is a top and end perspective view of the bucky presentation assembly of FIG. 1 (removed from the patient table), wherein the bucky is shown fully extended laterally but not pivoted upwardly;

FIG. 3 is an enlarged top and opposite end perspective view of a hinge of the bucky presentation assembly of Fig. 1;

FIG. 4 is a further enlarged side elevation view of a clock spring of the hinge of the bucky presentation assembly of the patient table of FIG. 1;

Like reference characters designate identical or corresponding components and units throughout the several views.

DETAILED DESCRIPTION OF EXEMPLARY EMBODIMENTS

Figure 1:
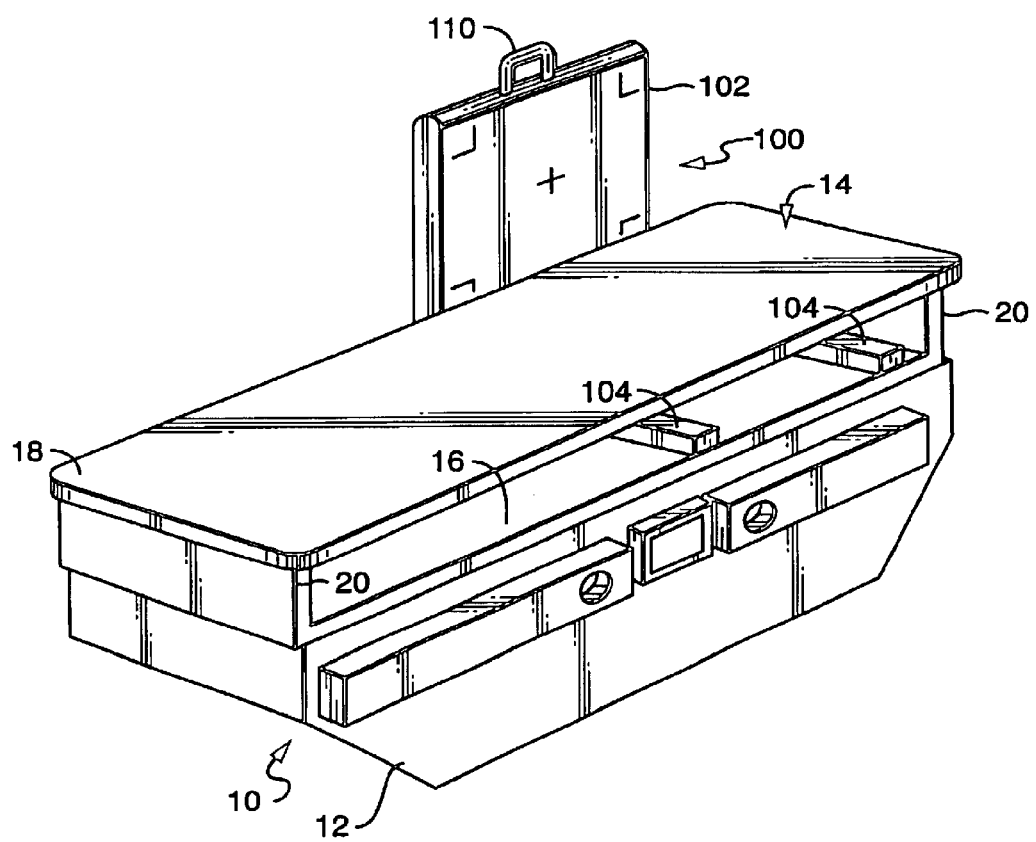
FIG. 1 is a top and end perspective view of an exemplary embodiment of a patient table constructed in accordance with the present disclosures and including a bucky presentation assembly, and wherein the bucky is shown fully extended laterally and fully pivoted to a raised position.

Referring to FIGS. 1 and 2 an exemplary embodiment of a bucky presentation assembly 100 constructed in accordance with the present disclosure is shown. The bucky presentation assembly 100 is provided as part of a patient table 10, as shown in FIG. 1, and can be used for, but is not limited to, positioning a bucky 102 with respect to a patient (not shown) supported on the patient table 10. Among other features and advantages, a new and improved bucky presentation assembly 100 constructed in accordance with the present disclosure allows specific portions of a patient lying or sitting on the patient table 10 to be quickly and accurately x-rayed. For example, the bucky presentation assembly 100 allows the bucky 102 to be positioned such that a hip of a patient lying or sitting on the table 10 can be quickly and accurately x-rayed.

Referring to FIG. 1, the patient table 10 includes a longitudinally extending, elongated table assembly 12 and a longitudinally extending, elongated pallet 14 positioned on the table assembly 12. The pallet 14 includes a lower portion 16, that is secured to the table assembly 12, and an upper portion 18 that is vertically spaced from the lower portion 16 and shaped and sized for a patient to lie thereon. The pallet 14 can include vertical end walls 20 for supporting the upper portion 18 above the lower portion 16. The pallet 14 may be made to be movable with respect to the table assembly 12, if desired.

The bucky presentation assembly 100 is positioned between the lower portion 16 and the upper portion 18 of the pallet 14 and includes at least one rail 104 secured to the pallet 14, a runner 106 slidably received on the rail 104, and a hinge 108 pivotally connecting the bucky 102 to the runner 106. FIG. 3 is an enlarged view of an exemplary embodiment of the hinge 108 of the bucky presentation assembly 100. As shown in FIG. 4, the hinge 108 can include a clock spring 114 biasing the hinge to an upwardly pivoted position in order to assist an operator in lifting the bucky 102.

In the exemplary embodiment shown, the rail comprises two spaced-apart, parallel rails 104 (although less than two, or more than two may be provided), and one of the runners 106 is slidably received on each rail. The rails 104 are secured to the lower portion 16 of the pallet 14, but could alternatively be secured to the upper portion 18 of the pallet 14. In yet another possible embodiment, the pallet 14 might simply include the upper portion 18 spaced from the table assembly 12, and the rails 104 could be secured to the table assembly 12 or the upper portion 18.

As shown in FIG. 1, the rails 104 of the bucky presentation assembly 100 extend in a lateral direction with respect to the table assembly 12, so that the bucky 102 can be extended from a side of the pallet 14. Alternatively, the rails could be oriented longitudinally on the pallet 14, such that the bucky 102 would extend longitudinally from an end of the pallet 14. The rails might also be oriented at an angle on the pallet 14, such that the bucky 102 would extend at an angle from a side or an end of the pallet 14. Although not shown, the rails 104 could be adapted and arranged for linear movement with respect to the pallet 14, such that all of the bucky presentation assembly 100 could be moved between opposing ends of the table 10.

As shown in FIGS. 1 and 2, the bucky 102 includes at least one handle 110 for maneuvering the bucky on the rails 104 and the hinges 108. In addition, the bucky 102 contains a removable detector 112. As shown best in FIG. 2, the bucky 102 is advantageously adapted so that the removable detector 112 can be inserted into the bucky 102 in one of a portrait view (as illustrated by the detector 112) or a landscape view position (as illustrated by the detector 112').

Figure 5:
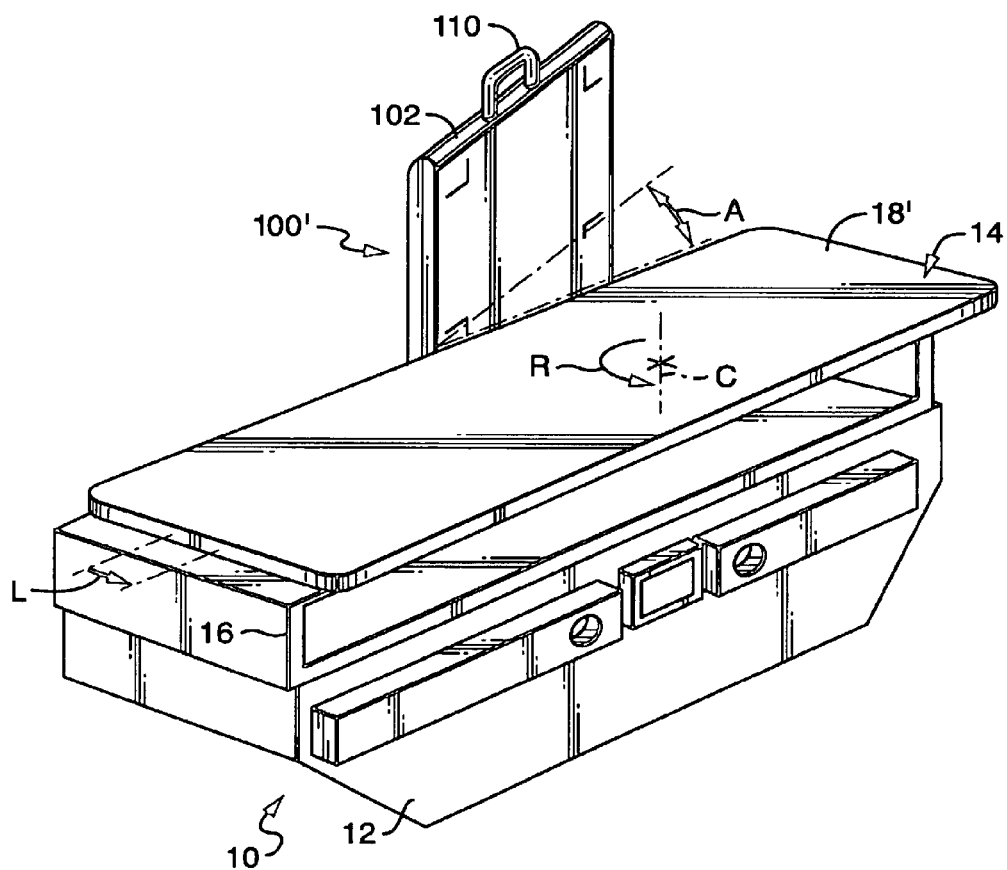
FIG. 5 is a top and side perspective view of another exemplary embodiment of a patient table constructed in accordance with the present disclosure and including a bucky presentation assembly, and wherein the bucky is shown fully extended laterally and fully pivoted upwardly to a raised position and the bucky presentation assembly is rotated, and a pallet of the table is shown laterally shifted to accommodate the rotated bucky presentation assembly.
Figure 6:
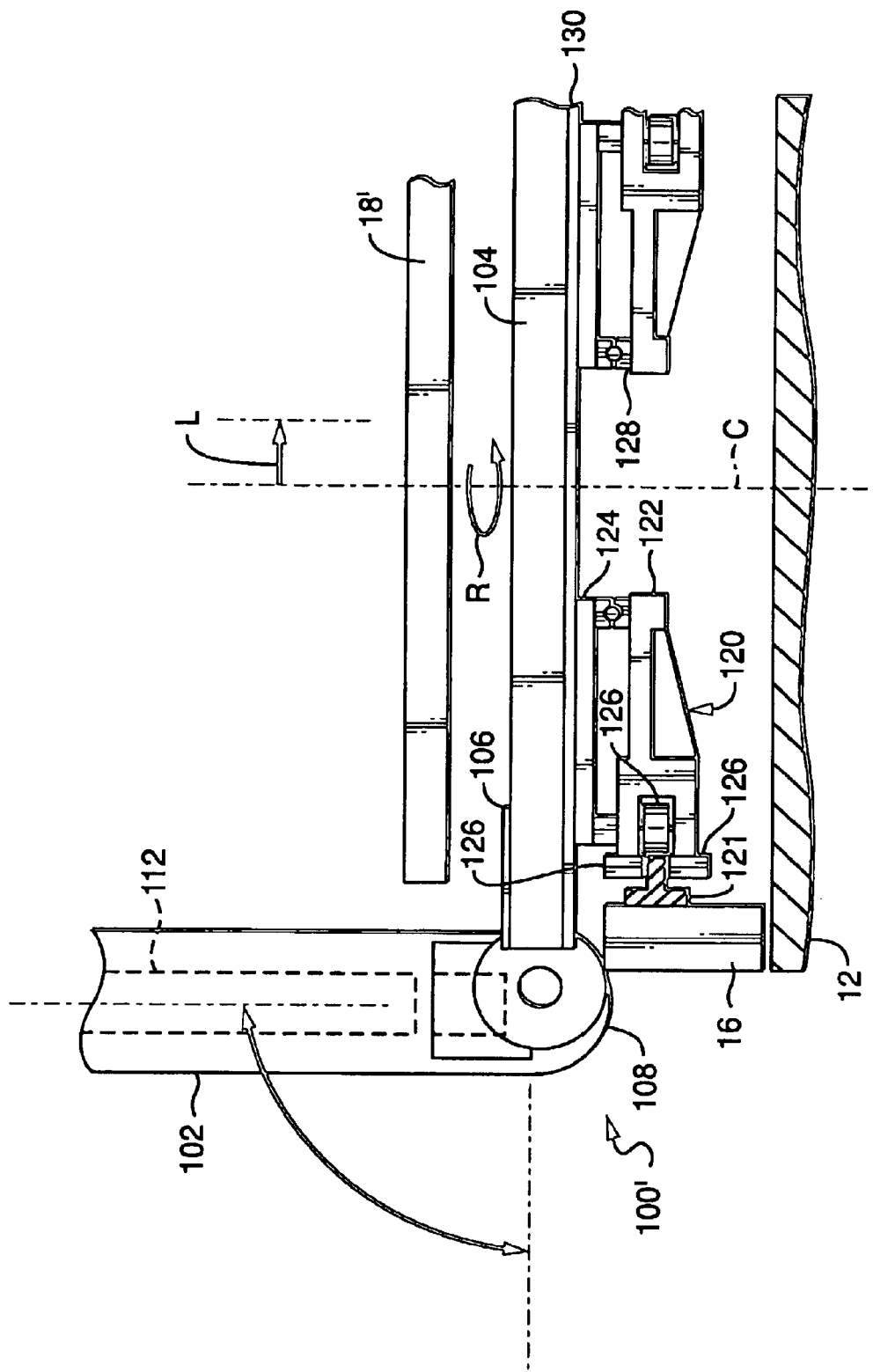
FIG. 6 is an enlarged end elevation view, partially in section, of a portion of the patient table of FIG. 5 showing a turntable rotatably supporting the bucky presentation assembly and the pallet positioned over the bucky presentation assembly and laterally shifted.
Figure 7:
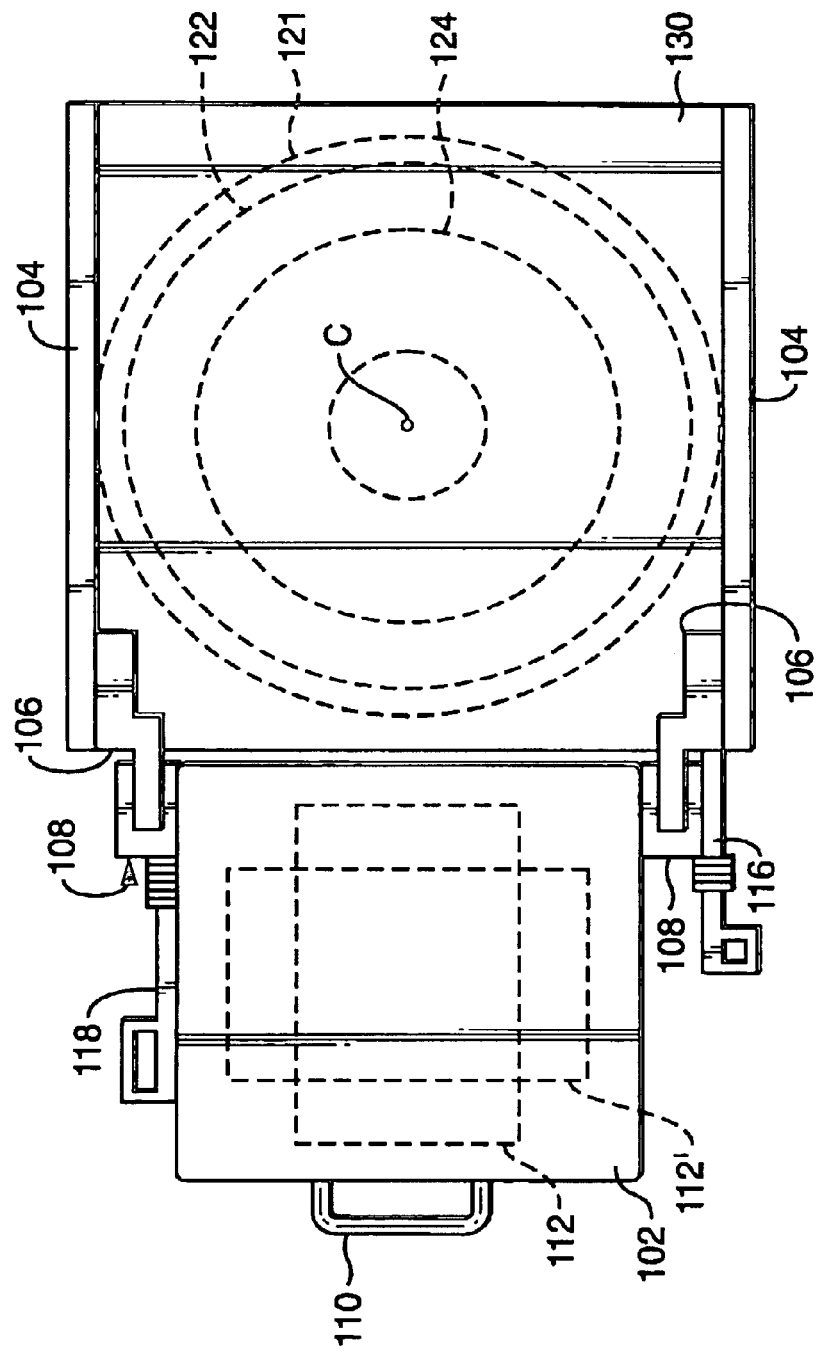
FIG. 7 is an enlarged top plan view of the bucky presentation assembly and the turntable of the patient table of FIG. 5.

Another exemplary embodiment of a table 10' and a bucky presentation assembly 100' are shown in FIGS. 5 and 6. The table 10' and the bucky presentation assembly 100' of FIGS. 5 and 6 are similar to the table 10 and the bucky presentation assembly 100 of FIG. 1, such that similar elements have the same reference characters. The bucky presentation assembly 100' of FIGS. 5 and 6, however, further includes a turntable 120, as shown in FIGS. 6 and 7, for allowing rotation of the bucky presentation assembly 100' (as illustrated by arrow R in FIGS. 5 and 6) to allow the bucky 102 to assume an angle (as illustrated by angle A in FIG. 5) with respect to the pallet 14. In addition, the table 10' includes an upper portion 18' of the pallet 14 that is laterally movable (as illustrated by arrow L in FIGS. 5 and 6) with respect to the lower portion 16 of the pallet 14 to accommodate rotation of the bucky presentation assembly 100'.

FIG. 7 is an enlarged top plan view of the bucky presentation assembly 100' and the turntable 120. As shown best in FIGS. 6 and 7, the turntable 120 includes a non-rotating portion 121 secured to the lower portion 16 of the pallet 14 of the table 10', and a first rotating portion 122 rotatably mounted on the non-rotating portion 121. The first rotating portion 122 can be rotatably mounted on the non-rotating portion 121, for example, using rollers 126, as shown in FIG. 6. The first rotating portion 122, therefore rotates about a center of rotation (as illustrated by line C in FIGS. 5, 6 and 7) with respect to the non-rotating portion 121 and the pallet 14 of the table 10'. The turntable 120 also includes a second rotating portion 124 that is rotatably mounted on the first rotating portion 122, using linear bearings 128 for example, so that the second rotating portion 124 also rotates about the center of rotation C. A platform 130 is secured to the second rotating portion 124 for rotation with the platform 130.

The rails 104 of the bucky presentation assembly 100' are secured to the platform 130, so that the bucky presentation assembly can be rotated on the turntable 120, in addition to being linearly moved on the rails 104, and pivoted up and down on the hinges 108. Moreover, the non-rotating portion 121 of the turntable 120 can be made to be linearly movable on the pallet of the table assembly 12.

As shown in FIG. 7, the bucky presentation assembly 100' can also include a slide locking mechanism 116 for locking the runners 106 in a fixed linear position on the rails 104, and a hinge-locking mechanism 118 for locking the hinges 108 in a desired pivoted position. Although not shown, the assembly 100' can further include a locking mechanism for locking the turntable 120 in a desired position, and stops for limiting rotation of the turntable.

It should be understood that the embodiments of the present disclosures described herein are merely exemplary and that a person skilled in the art may make variations and modifications to the embodiments described without departing from the spirit and scope of the present disclosures. All such equivalent variations and modifications are intended to be included within the scope of these disclosures as defined by the appended claims.

What is claimed is:

1. A patient table comprising:
 a table assembly; and
 a bucky presentation assembly including,
   at least one rail secured to the table assembly,
   a runner slidably received on each of the rails,
   a bucky,
   a hinge pivotally connecting the bucky to the runner, and
   a turntable including a non-rotating portion secured to the table assembly and a rotating portion rotatably mounted on the non-rotating portion, and wherein the rail of the bucky presentation assembly is secured to the rotating portion.

2. A patient table according to claim 1, wherein the at least one rail of the bucky presentation assembly comprises two spaced-apart, parallel rails.

3. A patient table according to claim 1, wherein the bucky includes at least one handle.

4. A patient table according to claim 1, wherein the bucky contains a removable detector in one of a landscape view or a portrait view position.

5. A patient table according to claim 1, wherein the bucky presentation assembly further includes a hinge locking mechanism for locking the hinge in a pivoted position.

6. A patient table according to claim 1, wherein the non-rotating portion of the turntable is linearly movable on the table assembly.

7. A patient table according to claim 1, wherein the rail of the bucky presentation assembly extends in a lateral direction with respect to the table assembly.

8. A patient table according to claim 7, wherein the rail of the bucky presentation assembly is movable in a longitudinal direction on the table assembly.

9. A patient table according to claim 1, further comprising a pallet including a lower portion secured to the table assembly and an upper portion spaced from the lower portion, wherein the bucky presentation assembly is positioned between the lower portion and the upper portion of the pallet.

10. A patient table according to claim 9, wherein the pallet is elongated and extends in a longitudinal direction, and the rail of the bucky presentation assembly extends laterally with respect to the pallet.

11. A patient table according to claim 10, wherein the upper portion of the pallet is movable in a lateral direction with respect to the lower portion of the pallet.

12. A patient table according to claim 1, wherein the rotating portion of the turntable comprises a first rotating portion rotatably mounted on the non-rotating portion and a second rotating portion rotatably mounted on the first rotating portion.

13. A patient table according to claim 12, wherein the first rotating portion is rotatably mounted on the non-rotating portion with rollers.

14. A patient table according to claim 12, wherein the second rotating portion is rotatably mounted on the first rotating portion with linear bearings.

15. A patient table comprising:
a table assembly; and
a bucky presentation assembly including,
   at least one rail secured to the table assembly,
   a runner slidably received on the rail,
   a bucky, and
   a hinge pivotally connecting the bucky to the runner and a clock spring biasing the hinge to an upwardly pivoted position.

16. A patient table comprising:
a table assembly; and
a bucky presentation assembly including,
   at least one rail secured to the table assembly,
   a runner slidably received on the rail,
   a slide locking mechanism for locking the runner in a fixed position on the rail,
   a bucky, and
   a hinge pivotally connecting the bucky to the runner.

17. A patient table comprising:
a table assembly; and
a bucky presentation assembly including,
   a bucky, and
   a turntable including a non-rotating portion secured to the table assembly and a rotating portion rotatably mounted on the non-rotating portion, and wherein the bucky is secured to the rotating portion.

18. A patient table comprising:
a table assembly; and
a bucky presentation assembly including,
   a turntable including a non-rotating portion secured to the table assembly and a rotating portion rotatably mounted on the non-rotating portion,
   at least one rail secured to the rotating portion,
   a bucky connected to the rail.

19. A patient table according to claim 18, wherein the bucky presentation assembly further comprises a runner slidably received on the rail and the bucky is secured to the runner such that the bucky can slide on the rail.

20. A patient table according to claim 18, wherein the bucky presentation assembly further comprises a hinge pivotally connecting the bucky to the runner so that the bucky can be pivoted up and down with respect to the rail.

* * * * *